US009259078B1

(12) United States Patent
Krug

(10) Patent No.: US 9,259,078 B1
(45) Date of Patent: Feb. 16, 2016

(54) TOOTHBRUSH AND TOOTHPASTE COMBINATION ASSEMBLY

(71) Applicant: Heidi Krug, Wheaton, IL (US)

(72) Inventor: Heidi Krug, Wheaton, IL (US)

( * ) Notice: Subject to any disclaimer, the term of this patent is extended or adjusted under 35 U.S.C. 154(b) by 0 days.

(21) Appl. No.: 14/587,667

(22) Filed: Dec. 31, 2014

(51) Int. Cl.
| A45D 44/18 | (2006.01) |
| A46B 11/00 | (2006.01) |
| A61C 15/00 | (2006.01) |
| A46B 15/00 | (2006.01) |
| A46B 17/04 | (2006.01) |
| A61C 15/02 | (2006.01) |

(52) U.S. Cl.
CPC ......... *A46B 11/0027* (2013.01); *A46B 15/0069* (2013.01); *A46B 17/04* (2013.01); *A61C 15/02* (2013.01)

(58) Field of Classification Search
CPC ...... A46B 5/00; A46B 11/00; A46B 11/0003; A46B 11/0006; A46B 11/001; A46B 11/0024; A46B 11/0027; A46B 11/0031; A46B 11/0089; A46B 15/00; A46B 15/0055; A46B 15/0069; A46B 15/0071; A46B 15/0073; A46B 17/04; A46B 17/08; A46B 2200/00; A46B 2200/10; A46B 2200/1066; A46B 11/0034; A61C 15/00; A61C 15/02; A61C 15/043; A61C 15/046; A61C 17/00; A61C 17/225; A61C 17/227; A61C 19/02; A61C 15/04; B05C 17/005; A45D 44/18; A45D 2200/25; B65D 35/30
USPC ......... 132/309, 308, 311, 321, 329, 313, 328; 206/581, 823, 63.5; 401/175, 171, 172
See application file for complete search history.

(56) References Cited

U.S. PATENT DOCUMENTS

| 1,336,390 | A | | 4/1920 | Sargery | |
| 1,711,183 | A | * | 4/1929 | Smith | 401/175 |
| 2,233,522 | A | * | 3/1941 | Fickle | 132/309 |
| 2,244,952 | A | * | 6/1941 | Kapelman | 222/387 |
| 2,601,244 | A | * | 6/1952 | Boulicault | 132/309 |
| 4,122,983 | A | * | 10/1978 | Jolly | 222/390 |
| 4,269,207 | A | | 5/1981 | Konrad et al. | |
| 4,288,169 | A | * | 9/1981 | McMenamin, IV | 401/175 |
| 4,322,497 | A | | 3/1982 | Hershberger | |
| 4,673,106 | A | * | 6/1987 | Fishman | 222/80 |
| 4,950,095 | A | * | 8/1990 | Picard | 401/191 |
| 5,046,212 | A | | 9/1991 | O'Conke | |
| 5,304,009 | A | | 4/1994 | Marshall | |
| 5,348,028 | A | * | 9/1994 | Gustavel | 132/309 |
| 5,769,553 | A | * | 6/1998 | Chaudhri et al. | 401/195 |
| 5,950,641 | A | | 9/1999 | Taveras | |
| D435,347 | S | | 12/2000 | Rumsey, Jr. | |
| D481,870 | S | | 11/2003 | Bochner | |
| 6,957,467 | B2 | * | 10/2005 | Cabedo-Deslierres et al. | 15/106 |
| 7,198,051 | B1 | * | 4/2007 | Festa | 132/309 |
| 7,478,960 | B2 | * | 1/2009 | Glover | 401/188 R |
| 8,015,982 | B2 | * | 9/2011 | Wilkinson | 132/309 |
| 8,695,611 | B2 | * | 4/2014 | Snedden et al. | 132/309 |
| 2005/0071939 | A1 | * | 4/2005 | Wong | 15/106 |
| 2006/0048790 | A1 | * | 3/2006 | Petner | 132/309 |
| 2008/0251097 | A1 | * | 10/2008 | Arreguin | 132/309 |
| 2011/0286783 | A1 | * | 11/2011 | Harden | 401/175 |

* cited by examiner

*Primary Examiner* — Vanitha Elgart

(57) ABSTRACT

A toothbrush and toothpaste combination assembly includes a housing that has a top wall, a bottom wall and a perimeter wall attached to and extending therebetween. A toothpaste is contained within the housing. A brush is coupled to the housing. A toothpick is coupled to the bottom wall of the housing. An actuating apparatus is provided. The actuating apparatus is in mechanical communication with the toothpaste. The actuating apparatus is actuated to urge the toothpaste through the brush. A top cap is removably coupled to the top wall to cover the brush. A bottom cap is removably coupled to the bottom wall to cover the toothpick.

8 Claims, 3 Drawing Sheets

TOOTHBRUSH AND TOOTHPASTE COMBINATION ASSEMBLY

BACKGROUND OF THE DISCLOSURE

1. Field of the Disclosure

The disclosure relates to toothpaste devices and more particularly pertains to a new toothpaste device for containing and dispensing a toothpaste onto a toothbrush.

2. Summary of the Disclosure

An embodiment of the disclosure meets the needs presented above by generally comprising a housing that has a top wall, a bottom wall and a perimeter wall attached to and extending therebetween. A toothpaste is contained within the housing. A brush is coupled to the housing. A toothpick is coupled to the bottom wall of the housing. An actuating apparatus is provided. The actuating apparatus is in mechanical communication with the toothpaste. The actuating apparatus is actuated to urge the toothpaste through the brush. A top cap is removably coupled to the top wall to cover the brush. A bottom cap is removably coupled to the bottom wall to cover the toothpick.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
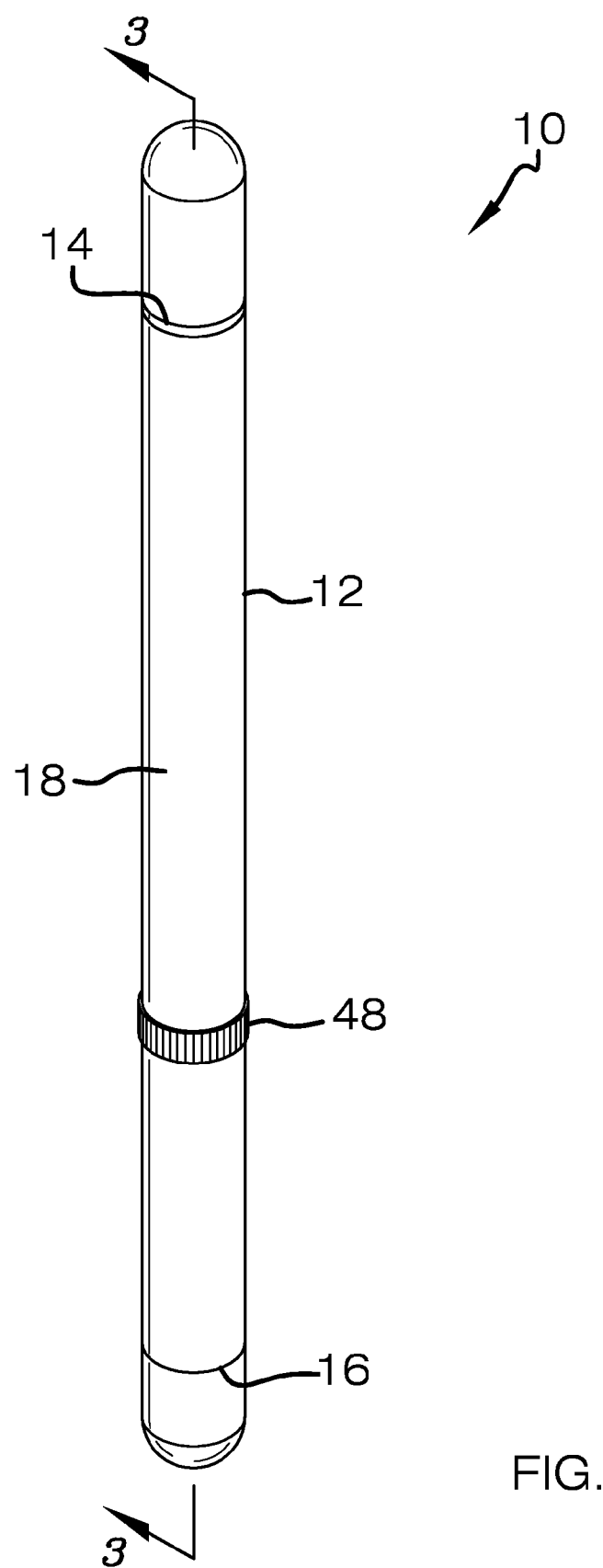
FIG. 1 is a perspective view of a toothbrush and toothpaste combination assembly according to an embodiment of the disclosure.
Figure 2:
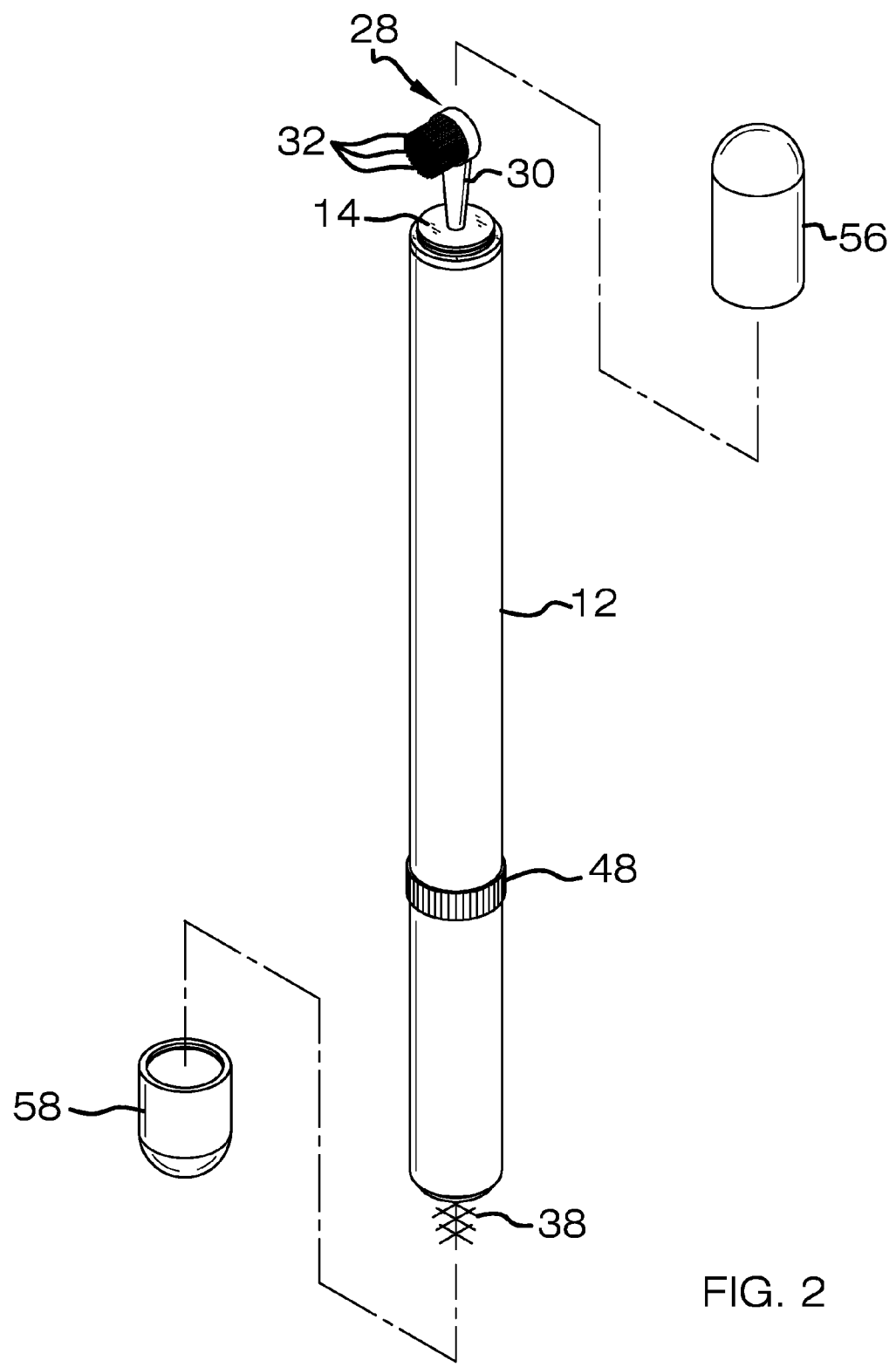
FIG. 2 is a front perspective view of an embodiment of the disclosure.
Figure 3:
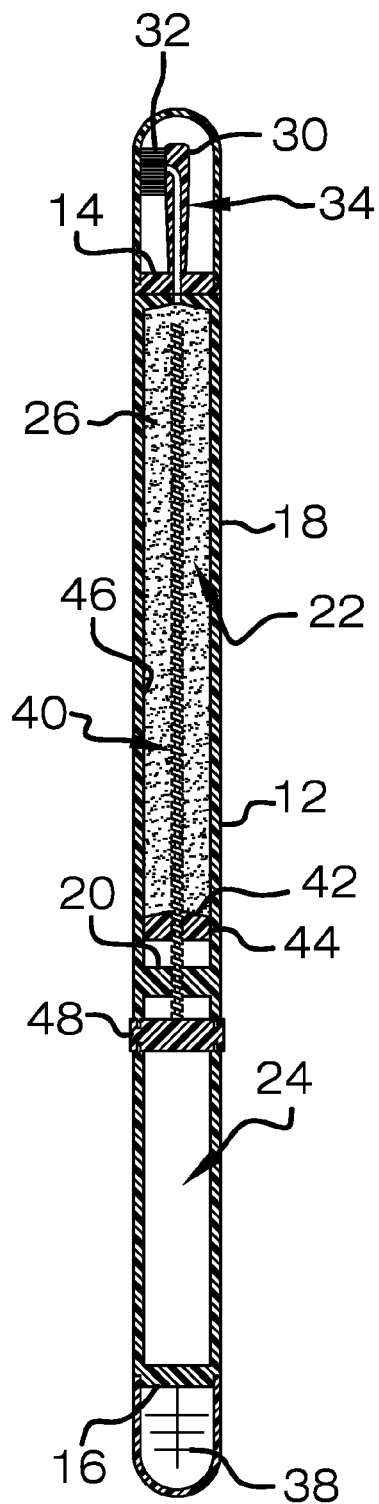
FIG. 3 is a cross sectional view taken along line 3-3 of FIG. 1 of an embodiment of the disclosure showing the assembly being full.
Figure 4:
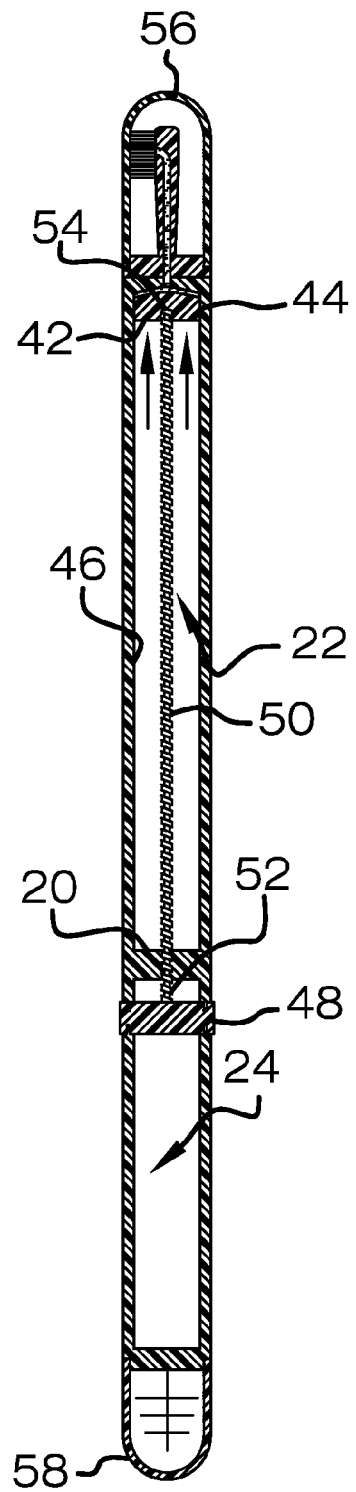
FIG. 4 is a cross sectional view taken along line 3-3 of FIG. 1 of an embodiment of the disclosure showing the assembly being empty.

With reference now to the drawings, and in particular to FIGS. 1 through 5 thereof, a new toothpaste device embodying the principles and concepts of an embodiment of the disclosure and generally designated by the reference numeral 10 will be described.

As best illustrated in FIGS. 1 through 5, the toothbrush and toothpaste combination assembly 10 generally comprises a housing 12 that has a top wall 14, a bottom wall 16 and a perimeter wall 18 attached to and extending therebetween. The housing 12 has a dividing wall 20 positioned within an interior of the housing 12 to define an upper section 22 and a lower section 24 of the housing 12. A toothpaste 26 is contained within the upper section 22. The toothpaste 26 may be a fluoridated toothpaste of any conventional design.

A brush 28 is coupled to the housing 12. The brush 28 comprises a stem 30 coupled to and extending upwardly from the top wall 14. A plurality of bristles 32 is coupled to and extends laterally away from the stem 30. A conduit 34 extends through the stem 30. The conduit 34 is in fluid communication with the upper section 22 and an extension of the stem 30. A toothpick 38 is coupled to the bottom wall 16 of the housing 12.

An actuating apparatus 40 is provided. The actuating apparatus 40 is in mechanical communication with the toothpaste 26. The actuating apparatus 40 is actuated to urge the toothpaste 26 through the conduit 34. The actuating apparatus 40 comprises a plunger 42 positioned between the toothpaste 26 and the dividing wall 20. The plunger 42 has an outer surface 44. The outer surface 44 of the plunger 42 abuts an inside surface 46 of the upper section 22, forming a fluid impermeable seal between the plunger 42 and the perimeter wall 18.

A knob 48 is rotatably coupled to the perimeter wall 18 of the housing 12. The knob 48 is positioned closer to the dividing wall 20 than the bottom wall 16. A screw 50 has a first end 52 and a second end 54. The first end 52 is coupled to the knob 48. The knob 48 selectively rotates the screw 50.

The screw 50 extends upwardly through the dividing wall 20 and upwardly through the upper section 22. The screw 50 extends through the plunger 42. The screw 50 threadably engages the plunger 42. Thus, the screw 50 urges the plunger 42 upwardly and downwardly in the upper section 22 when the knob 48 is rotated. The plunger 42 urges the toothpaste 26 through the conduit 34 when the knob 48 is rotated.

A top cap 56 is provided. The top cap 56 is removably coupled to the top wall 14 to cover the brush 28. A bottom cap 58 is provided. The bottom cap 58 is removably coupled to the bottom wall 16 to cover the toothpick 38.

In use, the knob 48 is rotated to dispense the toothpaste 26 onto the brush 28. The assembly 10 is utilized for travel purposes. The housing 12 prevents the toothpaste 26 from being inadvertently released. The assembly 10 is utilized in the convention of oral hygiene.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A toothbrush and toothpaste combination assembly comprising:

a housing having a top wall, a bottom wall and a perimeter wall attached to and extending therebetween, said housing having a dividing wall, said dividing wall being fixed within said housing;

a toothpaste contained within said housing;

a brush coupled to said housing;

a toothpick coupled to said bottom wall of said housing;

an actuating apparatus in mechanical communication with said toothpaste, said actuating apparatus being actuated to urge said toothpaste through said brush, said actuating apparatus comprising a plunger positioned between said toothpaste and said dividing wall;

a top cap removably coupled to said top wall to cover said brush;

a bottom cap removably coupled to said bottom wall to cover said toothpick; and a knob rotatably coupled to said perimeter wall of said housing, said knob being positioned closer to said fixed dividing wall than said bottom wall.

2. The assembly according to claim 1, further comprising said dividing wall being positioned within an interior of said housing to define an upper section and a lower section of said housing.

3. The assembly according to claim 2, wherein said brush comprising a stem coupled to and extending upwardly from said top wall.

4. The assembly according to claim 3, further comprising a plurality of bristles coupled to and extending laterally away from said stem.

5. The assembly according to claim 4, further comprising a conduit extending through said stem, said conduit being in fluid communication with said upper section and an extension of said stem.

6. The assembly according to claim 5, further comprising a screw having a first end and a second end, said first end being coupled to said knob, said knob selectively rotating said screw, said screw extending upwardly through said dividing wall and upwardly through said upper section.

7. The assembly according to claim 6, wherein said screw extending through said plunger, said screw urging said plunger upwardly and downwardly in said upper section when said knob is rotated, said plunger urging said toothpaste through said conduit when said knob is rotated.

8. A toothbrush and toothpaste combination assembly comprising:

a housing having a top wall, a bottom wall and a perimeter wall attached to and extending therebetween, said housing having a dividing wall positioned within an interior of said housing to define an upper section and a lower section of said housing, said dividing wall being fixed within said housing;

a toothpaste contained within said upper section;

a brush coupled to said housing, said brush comprising:
  a stem coupled to and extending upwardly from said top wall;
  a plurality of bristles coupled to and extending laterally away from said stem; and
  a conduit extending through said stem, said conduit being in fluid communication with said upper section and an extension of said stem;

a toothpick coupled to said bottom wall of said housing;

an actuating apparatus in mechanical communication with said toothpaste, said actuating apparatus being actuated to urge said toothpaste through said conduit, said actuating apparatus comprising:
  a plunger positioned between said toothpaste and said dividing wall;
  a knob rotatably coupled to said perimeter wall of said housing, said knob being positioned closer to said fixed dividing wall than said bottom wall; and
  a screw having a first end and a second end, said first end being coupled to said knob, said knob selectively rotating said screw, said screw extending upwardly through said dividing wall and upwardly through said upper section, said screw extending through said plunger, said screw urging said plunger upwardly and downwardly in said upper section when said knob is rotated, said plunger urging said toothpaste through said conduit when said knob is rotated;

a top cap removably coupled to said top wall to cover said brush; and a bottom cap removably coupled to said bottom wall to cover said toothpick.

\* \* \* \* \*